US009650613B2

(12) United States Patent
Park et al.

(10) Patent No.: US 9,650,613 B2
(45) Date of Patent: May 16, 2017

(54) CELL STRAIN HAVING INCREASED VIRUS PRODUCTION ABILITY AND PRODUCTION METHOD THEREFOR

(71) Applicant: IMMUNOMAX CO., LTD., Seoul (KR)

(72) Inventors: Se-Ho Park, Seoul (KR); Eunbi Yi, Seoul (KR)

(73) Assignee: IMMUNOMAX CO., LTD., Seoul (KR)

( * ) Notice: Subject to any disclaimer, the term of this patent is extended or adjusted under 35 U.S.C. 154(b) by 0 days.

(21) Appl. No.: 14/773,741

(22) PCT Filed: Dec. 27, 2013

(86) PCT No.: PCT/KR2013/012263

§ 371 (c)(1),
(2) Date: Sep. 8, 2015

(87) PCT Pub. No.: WO2014/142433

PCT Pub. Date: Sep. 18, 2014

(65) Prior Publication Data

US 2016/0326498 A1 Nov. 10, 2016

(30) Foreign Application Priority Data

Mar. 13, 2013 (KR) ........................ 10-2013-0026767
Oct. 1, 2013 (KR) ........................ 10-2013-0117325

(51) Int. Cl.

*A01N 63/00* (2006.01)
*C12N 7/00* (2006.01)
*C12N 5/071* (2010.01)
*C12N 15/10* (2006.01)

(52) U.S. Cl.

CPC ............. *C12N 7/00* (2013.01); *C12N 5/0686* (2013.01); *C12N 15/102* (2013.01); *C12N 2510/00* (2013.01); *C12N 2510/02* (2013.01); *C12N 2710/16634* (2013.01); *C12N 2710/16651* (2013.01); *C12N 2760/16134* (2013.01); *C12N 2760/16151* (2013.01)

(58) Field of Classification Search

None
See application file for complete search history.

(56) References Cited

U.S. PATENT DOCUMENTS

2012/0083035 A1 4/2012 Spayd et al.

FOREIGN PATENT DOCUMENTS

KR 1020110029181 A 3/2011
KR 1020120033334 A 4/2012
KR 1020120103737 A 9/2012
WO 2005014862 A1 2/2005
WO 2008127261 A1 10/2008
WO 2011006823 A1 1/2011

OTHER PUBLICATIONS

Urata et al. Viruses 2012;4:2049-79.*
Hammonds et al. Mole Biol Intl 2012, Article ID 424768.*
Gupta et al. PloS Pathog 2009;5:e1000443.*
Swieckie et al. J Immunol 2012;188:2488-92.*
Fiore, A., et al., "Chapter 17: Inactivated influenza vaccines", "Vaccines 6th edition", Sep. 2, 2012, pp. 257-293, Publisher: Elsevier, Published in: New York/USA.
Luke, C., et al., "Chapter 18: Influenza vaccine-live", "Vaccines 6th edition", Sep. 2, 2012, pp. 294-311, Publisher: Elsevier, Published in: New York/USA.
Treanor, J., "Chapter 167: Influenza (Including Avian Influenza and Swine Influenza)", "In Principles and Practice of Infectious Diseases, 8th Edition", Aug. 28, 2014, pp. 2000-2024, Publisher: Saunders, Published in: Philadelphia/USA.
Jang, J., et al., "Overespression of Newcastle disease virus (NDV) V protein enhances NDV production kinetics in chicken embryo fibroblasts", "Appl. Microbiol. Biotechnol", Sep. 3, 2009, pp. 1509-1520, vol. 85.
Jones, P., et al., "Bone marrow stromal cell antigen 2 (BST-2) restricts mouse mammary tumor virus (MMTV) replication in vivo", "Retrovirology", Jan. 27, 2012, pp. 1-12, vol. 9, No. 10.
Na, H., et al., "Interactions between human immunodeficiency virus (HIV)-1 Vpr expression and innate immunity influence neurobirulence", "Retrovirology", Jun. 6, 2011, pp. 1-17, vol. 8, No. 44.
Pan, X., et al., "BST2/Tetherin Inhibits Dengue Virus Release from Human Hepatoma Cells", "PLOS ONE", Dec. 7, 2012, pp. e51033 1-7, vol. 7, No. 12.
Van Damme, N., et al., "The interferon-induced protein BST-2 restricts HIV-1 release and is downregulated from the cell surface by the viral Vpu protein", "Cell Host & Microbe", Mar. 13, 2008, pp. 245-252, vol. 3.
Watanabe, R., et al., "Influenza virus is not restricted by tetherin whereas influenza VLP production is restricted by tetherin", "Virology", May 28, 2011, pp. 50-56, vol. 417.
Borden, E.C., et al., "Interferon-Stimulated Genes and Their Protein Products: What and How?", "Journal of Interferon & Cytokine Research", Jan. 2011, vol. 31, No. 1, pp. 1-4; DOI 10.1089/jir.2010.0129.

* cited by examiner

*Primary Examiner* — Janice Li
(74) *Attorney, Agent, or Firm* — Hultquist, PLLC; Steven J. Hultquist

(57) ABSTRACT

The present invention relates to a cell line having an increased ability to produce virus and a method for preparing thereof, and more particularly, to a cell line that has an increased ability to produce virus, due to the loss of the function of the Bst-2 (tetherin) gene, and to a production method thereof. According to the present invention, a cell line lacking the function of the Bst-2 gene has an excellent ability to produce virus, compared to a wild-type cell line. Thus, when the mutant cell line is used as a virus-producing cell line, the production yield of virus can be increased. In addition, the mutant cell line can be used for the production and research of vaccines for preventing and treating viral diseases.

21 Claims, 13 Drawing Sheets

CELL STRAIN HAVING INCREASED VIRUS PRODUCTION ABILITY AND PRODUCTION METHOD THEREFOR

CROSS-REFERENCE TO RELATED APPLICATIONS

This application is a U.S. national phase under the provisions of 35 U.S.C. §371 of International Patent Application No. PCT/KR13/12263 filed Dec. 27, 2013, which in turn claims priority of Korean Patent Application No. 10-2013-0026767 filed Mar. 13, 2013 and Korean Patent Application No. 10-2013-0117325 filed Oct. 1, 2013. The disclosures of such international patent application and Korean priority patent applications are hereby incorporated herein by reference in their respective entireties, for all purposes.

TECHNICAL FIELD

The present invention relates to a cell line having an increased ability to produce virus and a method for preparing thereof, and more particularly, to a cell line that has an increased ability to produce virus, due to the loss of the function of the Bst-2 (tetherin) gene, and to a production method thereof.

BACKGROUND ART

Influenza is an acute febrile disease caused by respiratory infection with influenza virus. Influenza viruses are classified into types A, B and C based on their core proteins. Hosts, epidemiology and clinical features somewhat differ between influenza types A, B and C. Influenza viruses are spherical viruses having a diameter of 80-120 nm, and are divided into various subtypes based on the antigenic properties of the hemagglutinin (HA) and neuraminidase (NA) glycoproteins on the surface of the virus. In the case of type A influenza, 16 HA subtypes (H1 to H16) and 9 NA subtypes (N1 to N9) have been identified. Thus, theoretically, 144 subtypes of influenza A virus (e.g., H1N1, H1N2, etc.) exist (Treanor J. J. et al., *In Principles and Practice of Infectious Diseases,* 2060-85, 2005).

Influenza vaccines include inactivated vaccines and live vaccines. Inactivated vaccines are produced by purifying viruses cultured in embryonated eggs and inactivating the cultured viruses with formalin or the like. Inactivated vaccines include inactivated whole-virus vaccines, split vaccines produced by disrupting viral envelopes with ether or the like, subunit vaccines obtained by purifying the hemagglutinin and neuraminidase components, etc. As live vaccines, live attenuated influenza vaccines (LAIVs) have been developed and used. Because whole virus vaccines cause side effects in infants, these vaccines are hardly used in many countries, including Korea, and are used only in some countries. However, component vaccines such as split vaccines or subunit vaccines are highly safe and have recognized effects, and thus have been most frequently used. In addition, vaccines containing an immune adjuvant (such as MF-59) for enhancing immune responses, or virosome vaccines that form virus-like vesicles, have been developed and used in some countries (Bridges C. B. et. al., In Vaccines, 259-290, 2008; Belshe R. B. et. al., In Vaccines, 291-309, 2008).

Until now, for the production of viruses for producing vaccines against influenza, a method of inoculating seed virus into fertilized eggs and culturing the inoculated virus has been used (Korean Patent Laid-Open Publication No. 10-2012-0103737A). However, this method has very low efficiency due to problems, including the security of supply of fertilized eggs, allergic induction, and viral propagation. To obtain specific pathogen-free eggs that are used for vaccine production, chickens should be raised in germ-free facilities completely isolated from the outside in a state in which an antibiotic and a vaccine are not administered to the chickens, and fertilized eggs should be produced from the chickens. The produced pathogen-free eggs are hatched in a hatchery for about 10 days, after which virus is inoculated into the embryo or allantoic fluid of the eggs by a syringe needle or the like. The inoculated virus is cultured for 3 days after inoculation, and then the cultured virus is recovered and subjected to a purification process. The virus prepared by such procedures is subjected to an inactivation process in some cases, and then an adjuvant for inducing an effective immune response, a stabilizer, a preservative and the like are added thereto, thereby producing a vaccine. The produced vaccine is filled into individual vials or syringes, after which it is inspected, packaged and shipped. In the case of Japanese encephalitis virus, the virus is also inoculated into the brain of suckling mice in addition to fertilized eggs and cultured.

In such conventional vaccine production methods, there is difficulty in expanding production facilities. For example, additional supply of fertilized eggs as a raw material is required to expand production processes that use fertilized eggs, and for this supply, chicken farming facilities free of germs should be expanded. Because chickens raised in these facilities are immunologically very weak, these chickens are difficult to raise, compared to general chickens, and need to be thoroughly controlled. Thus, there are many limits to the expansion of such facilities, in spatial or economic terms. In addition, there may be difficulty in steadily supplying pathogen-free eggs when avian infectious diseases such as avian influenza (AI) or Newcastle disease (ND) are prevalent.

In an attempt to overcome such conventional problems, methods of producing vaccines by animal cell culture have received attention long ago (Korean Patent Laid-Open Publication No. 10-2012-0033334). These methods include a method of producing a vaccine by culturing a large amount of animal cells under germ-free conditions and infecting the cultured animal cells with virus, a method of producing only antigens, which induce antibody production, by a genetic engineering method, etc. The biggest advantage of the method of producing vaccines by animal cell culture is that the production scale can be expanded. Specifically, the production scale can be expanded as desired according to the culture scale of animal cells that are used as a raw material for vaccine production.

However, despite such many advantages, the production of vaccines by animal cell culture is not easy to achieve. This is because the initial investment is too high, a personal infrastructure for smoothly performing this production is insufficient, and the yield per unit volume is somewhat lower than that of the use of fertilized eggs or animals. In order to overcome low yields per unit volume when producing vaccines using animal cells, there were some attempts to develop excellent host animal cell lines using genetic engineering techniques (fang J. et al., Appl. Microbiol. Biotechnol, 85:1509-1520, 2010), but such attempts still remain at an insufficient level. Thus, to optimize virus production, the identification of a virus-producing cell line, the improvement of culture conditions and the improvement of infection conditions are required.

Examples of typical cell lines that are currently used for the production of viral vaccines include MDCK (cells derived from the Madin-Darby canine kidney), PerC6 (cells derived from human embryonic retinal cells genetically modified by inserting the E1 genes from the human adenovirus type 5) developed by CRUCELL (Netherland), VERO (cells derived from epithelial cells of kidney from African green monkey (*Cercopithecus aethiops*) isolate at the Chiba University in Chiba, Japan), and BHK21 (Cells immortalized from baby hamster kidney cells).

Meanwhile, when virus infects the body, the proliferation of the virus in the infected cells occurs, and the proliferated virus particles bud out through the cell membrane to infect other surrounding cells. In part of the defense mechanism of cells against viral infection, Bst-2 gene is expressed in the cell membrane. Bst-2 has cell membrane-binding sites at both the N-terminus and the C-terminus, and thus is expressed in the cell membrane in a form in which the middle is lifted, like a bridge. The C-terminus of Bst-2 is located in the lipid raft region of the cell membrane, and the N-terminus is located in the non-lipid raft region.

The function of the C-terminal region fixed to the lipid raft region is not yet known. Meanwhile, when virus buds from the lipid raft region to the outside of the cells, Bst-2 inhibits the passage of virus particles through the cell membrane by its region fixed to the non-lipid raft region. For this defense mechanism of mammal cells, some viruses produce a protein that promotes the degradation of the Bst-2 gene in order to avoid this mechanism of the host cells. This paradoxically indicates that the function of the Bst-2 gene strongly contributes to the inhibition of production of virus. However, not all viruses have this function, and some viruses (particularly HIV virus) have a function of promoting the degradation of the Bst-2 gene by the Vpu gene, and other most viruses do not have the avoidance mechanism that targets the Bst-2 gene.

Thus, in order to efficiently produce a large amount of virus and use the produced virus for vaccine production, there is a need for the development of a technology capable of inactivating or inhibiting the function of the Bst-2 gene in animal cells for culturing a virus that does not promote the degradation of the Bst-2 gene.

Accordingly, the present inventors have made extensive efforts to develop a method for increasing the ability of a host cell to produce a virus, and as a result, have found that, when the function of the Bst-2 gene in a cell is lacked, a virus-producing cell line that has an increased ability to produce virus, due to the promotion of extracellular release of virus and the reduction of apoptosis, can be produced, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

It is an object of the present invention to provide a method for preparing a virus-producing mutant cell line that is reduced from virus-induced apoptosis.

Another object of the present invention is to provide a virus-producing mutant cell line having an increased ability to produce virus.

Still another object of the present invention is to provide a method of producing virus using the virus-producing mutant cell line having an increased ability to produce virus.

Yet another object of the present invention is to provide a method of producing a vaccine against viral disease using the virus-producing mutant cell line having an increased ability to produce virus.

To achieve the above objects, the present invention provides a method for preparing a virus-producing mutant cell line that is reduced from virus-induced apoptosis, the method comprising mutating Bst-2 gene in a virus-producing cell line.

The present invention also provides a virus-producing mutant cell line which lacked the function of Bst-2 gene in a cell line having an ability to produce virus, wherein the mutant cell line having an increased ability to produce virus by lacking the function of said Bst-2 gene.

The present invention also provides a virus-producing mutant cell line in which introduced a mutated Bst-2 gene in a virus-producing cell line that expresses no Bst-2, wherein the mutant cell line having an increased ability to produce virus by introducing the mutated Bst-2 gene.

The present invention also provides a method for producing a desired virus, the method comprising the steps of: (a) infecting a mutant cell line, which has an increased ability to produce virus, with a desired virus; and (b) culturing the cell line infected with the desired virus, and then centrifuging the supernatant of the culture to recover the desired virus.

The present invention also provides a method for producing a vaccine against viral disease, the method comprising the steps of: (a) infecting a mutant cell line, which has an increased ability to produce virus, with a desired virus; (b) culturing the cell line infected with the desired virus, and then centrifuging the supernatant of the culture to recover the desired virus; and (c) attenuating or inactivating the recovered virus.

Other features and embodiments of the present invention will be more apparent from the following detailed descriptions and the appended claims.

BEST MODE FOR CARRYING OUT THE INVENTION

Figure 1:
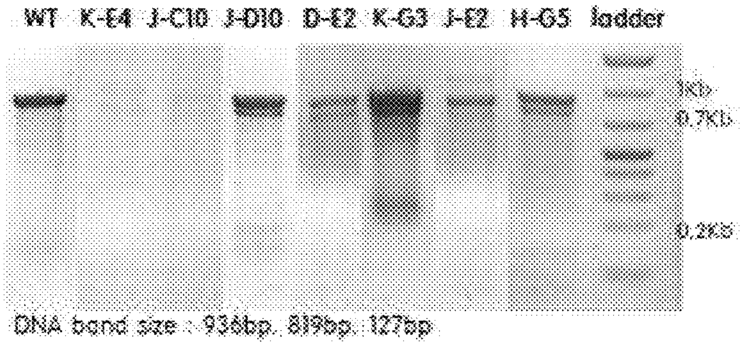
FIG. 1 shows the results of PCR (polymerase chain reaction) products of MDCK cell line having a mutated Bst-2 gene by electrophoresis.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, it was found that a cell line having an increased ability to produce virus can be produced by lacking the function of Bst-2 gene in a cell so as to enable virus to be released from the host cell without being interfered with by the host cell and to enable the apoptosis of the cell to be reduced.

As used herein, the term "ability to produce" means that a virus that proliferated in a virus-producing cell line during the survival of the cell is released into a culture medium to increase the viral titer of the culture medium.

As used herein, the term "lack of function" means mutating one or more nucleotides of Bst-2 gene in a cell and releasing virus from the cell. Preferably, the term means a deletion or insertion of the exon 1 region of the Bst-2 gene, a knock-out, or a silencing of the Bst-2 gene.

As used herein, the term "virus" means virus that can cause a disease in humans or animals. Preferably, the term means influenza virus. More preferably, it means one selected from the group consisting of P/H1N1, A/H1N1 and A/H3N2.

In the present invention, "virus" is not limited to influenza virus, and may include other disease-causing viruses, preferably, Herpes simplex virus.

As used herein, the term "apoptosis" means a process in which a cell actively consumes the bioenergy ATP, leading to death. A typical apoptotic process comprises the shrinkage of cells, the regular cleavage of DNA, and the fragmentation of the cell membrane. Apoptosis can be induced when cells cannot maintain their normal function due to abnormal cell division, radiation, UV light, bacterial infection or viral infection.

In one aspect, the present invention is directed to a virus-producing mutant cell line which lacked the function of Bst-2 gene in a cell line having an ability to produce virus, wherein the mutant cell line having an increased ability to produce virus by lacking the function of said Bst-2 gene.

As the cell line having virus production ability, any cell line that is used in the development of influenza vaccines may be used. Preferably, an animal cell line may be used, and more preferably, MDCK cells, VERO cells or fibroblasts may be used.

The MDCK (Madin-Darby canine kidney) cells that are used in the present invention are epidermis-like cells obtained from the canine kidney, and the VERO cells are cells obtained from the monkey kidney. The two cell lines show sensitivity to hepatitis virus, vaccinia virus and influenza virus, and thus are most frequently used in viral research.

The mutant cell line may have an insertion, deletion, duplication, inversion, substitution or translocation of a portion of the Bst-2 gene, a deletion of the whole of the Bst-2 gene, or a silencing of the Bst-2 gene.

The mutant cell line may have a deletion of 1-15 nucleotides from the exon 1 region of the Bst-2 gene or an insertion of 1-15 nucleotides in the exon 1 region.

The mutant cell line may have a deletion of 1-4 nucleotides from positions 45 to 50 of the exon 1 region of the Bst-2 gene or an insertion of 1-3 nucleotides in positions 45 to 50 of the exon 1 region.

The mutant cell line may have a deletion of 1-12 nucleotides from positions 116 to 130 of the exon 1 region of the Bst-2 gene.

The mutant cell line may have a deletion of nucleotides from positions 4 to 90 of the exon 1 region of the Bst-2 gene.

In the present invention, 1-15 nucleotides were inserted into or deleted from the exon 1 region of a Bst-2 gene, represented by SEQ ID NO: 1 or 2, in order to produce a mutant cell line.

In an example of the present invention, one or more nucleotides were inserted into or deleted from the exon 1 region of the MDCK Bst-2 gene, represented by SEQ ID NO: 1, to produce a mutant cell line that comprises a mutated allele and that has an increased ability to produce virus.

```
SEQ ID NO: 1:
ATGGCACCTACGCTTTACCACTACTACTGGCCTGTGCCCATAACTG

ACGAGTCAGAGTCAATGTCATCAAGTCAGAAGCTGAGCTGGCTGGA

GTGGCTGGGCATCTTGGGGATCCCAGTGGTGATGGGTCTGTCTGTG

GCTCTGATCATCTTTGTTGTCAAGACCAACAGCAAAGCCTGCGGGG

ATGGCCTCCTAGTAGAGCAGGAGTGTCACAATGTCACCAGCCTCCT

GGAGCGCCAACTAACCCAAACCCGGCAAGCGTTACAGGGGACCATG

GACCAGGCTACCACCTGCAACAAGACTGTG
```

In another example of the present invention, mutant cell lines lacking the function of the Bst-2 gene were produced by deleting 1-4 nucleotides from or inserting 1-3 nucleotides into positions 45 to 50 of the exon 1 region of the Bst-2 gene. These mutant cell lines may include cell lines having any one of nucleotide sequences of SEQ ID NOS: 3 to 8, and preferably, may be K-E4, J-C10, J-D10, D-E2, K-G3, J-E2 and H-G5.

SEQ ID NO: 3:
ATGGCACCTACGCTTTACCACTACTACTGGCCTGTGCCCATAACTG

AAGTCAGAGTCAATGTCATCAAGTCAGAAGCTGAGCTGGCTGGAGT

GGCTGGGCATCTTGGGGATCCCAGTGGTGATGGGTCTGTCTGTGGC

TCTGATCATCTTTGTTGTCAAGACCAACAGCAAAGCCTGCGGGGAT

GGCCTCCTAGTAGAGCAGGAGTGTCACAATGTCACCAGCCTCCTGG

AGCGCCAACTAACCCAAACCCGGCAAGCGTTACAGGGGACCATGGA

CCAGGCTACCACCTGCAACAAGACTGTG

SEQ ID NO: 4:
ATGGCACCTACGCTTTACCACTACTACTGGCCTGTGCCCATAACAC

GAGTCAGAGTCAATGTCATCAAGTCAGAAGCTGAGCTGGCTGGAGT

GGCTGGGCATCTTGGGGATCCCAGTGGTGATGGGTCTGTCTGTGGC

TCTGATCATCTTTGTTGTCAAGACCAACAGCAAAGCCTGCGGGGAT

GGCCTCCTAGTAGAGCAGGAGTGTCACAATGTCACCAGCCTCCTGG

AGCGCCAACTAACCCAAACCCGGCAAGCGTTACAGGGGACCATGGA

CCAGGCTACCACCTGCAACAAGACTGTG

SEQ ID NO: 5:
ATGGCACCTACGCTTTACCACTACTACTGGCCTGTGCCCATAACTA

GTCAGAGTCAATGTCATCAAGTCAGAAGCTGAGCTGGCTGGAGTGG

CTGGGCATCTTGGGGATCCCAGTGGTGATGGGTCTGTCTGTGGCTC

TGATCATCTTTGTTGTCAAGACCAACAGCAAAGCCTGCGGGGATGG

CCTCCTAGTAGAGCAGGAGTGTCACAATGTCACCAGCCTCCTGGAG

CGCCAACTAACCCAAACCCGGCAAGCGTTACAGGGGACCATGGACC

AGGCTACCACCTGCAACAAGACTGTG

SEQ ID NO: 6:
ATGGCACCTACGCTTTACCACTACTACTGGCCTGTGCCCATAACTG

AGTCAGAGTCAATGTCATCAAGTCAGAAGCTGAGCTGGCTGGAGTG

GCTGGGCATCTTGGGGATCCCAGTGGTGATGGGTCTGTCTGTGGCT

CTGATCATCTTTGTTGTCAAGACCAACAGCAAAGCCTGCGGGGATG

GCCTCCTAGTAGAGCAGGAGTGTCACAATGTCACCAGCCTCCTGGA

GCGCCAACTAACCCAAACCCGGCAAGCGTTACAGGGGACCATGGAC

CAGGCTACCACCTGCAACAAGACTGTG

SEQ ID NO: 7:
ATGGCACCTACGCTTTACCACTACTACTGGCCTGTGCCCATAACGA

GTCAGAGTCAATGTCATCAAGTCAGAAGCTGAGCTGGCTGGAGTGG

CTGGGCATCTTGGGGATCCCAGTGGTGATGGGTCTGTCTGTGGCTC

TGATCATCTTTGTTGTCAAGACCAACAGCAAAGCCTGCGGGGATGG

CCTCCTAGTAGAGCAGGAGTGTCACAATGTCACCAGCCTCCTGGAG

CGCCAACTAACCCAAACCCGGCAAGCGTTACAGGGGACCATGGACC

AGGCTACCACCTGCAACAAGACTGTG

SEQ ID NO: 8:
ATGGCACCTACGCTTTACCACTACTACTGGCCTGTGCCCATAACTG

ACGACGAGTCAGAGTCAATGTCATCAAGTCAGAAGCTGAGCTGGCT

GGAGTGGCTGGGCATCTTGGGGATCCCAGTGGTGATGGGTCTGTCT

GTGGCTCTGATCATCTTTGTTGTCAAGACCAACAGCAAAGCCTGCG

GGGATGGCCTCCTAGTAGAGCAGGAGTGTCACAATGTCACCAGCCT

CCTGGAGCGCCAACTAACCCAAACCCGGCAAGCGTTACAGGGGACC

ATGGACCAGGCTACCACCTGCAACAAGACTGTG

In still another example of the present invention, a mutant cell line comprising a mutated allele and having an increased ability to produce virus was produced by deleting nucleotides from the exon 1 region of the VERO Bst-2 gene, represented by SEQ ID NO: 2.

SEQ ID NO: 2:
ATGGCACCTATTTTGTATGACTATTGCAAAATGCCCATGGATGACA

TTTGCAAGGAAGACAGGGACAAGTGCTGTAAACTGGCCGTAGGAAT

TCTGGGGCTCCTGGTCATAGTGCTTCTGGGGGTGCCCCTGATTTTC

TTCATCATCAAGGCCAACAGCGAGGCCTGCCAGGATGGCCTCCGGG

CAGTGATGGAGTGTCACAATGTCACCTATCTCCTGCAACAAGAGCT

GGCCGAGGCCCAGCGGGGCTTTCGGGACGCAGAGGCCCAGGCTGTC

ACCTGCAACCAGACTGTG

In still another example of the present invention, mutant cell lines lacking the function of the Bst-2 gene were produced by deleting 1-12 nucleotides from positions 116 to 130 of the exon 1 region of the Bst-2 gene. These mutant cell lines may include cell lines having any one of nucleotide sequences of SEQ ID NOS: 9 and 10, and preferably, may be D-D8 and G-D5.

SEQ ID NO: 9:
ATGGCACCTATTTTGTATGACTATTGCAAAATGCCCATGGATGACA

TTTGCAAGGAAGACAGGGACAAGTGCTGTAAACTGGCCGTAGGAAT

TCTGGGGCTCCTGGTCATAGTGCCCCTGATTTTCTTCATCATCAAG

GCCAACAGCGAGGCCTGCCAGGATGGCCTCCGGGCAGTGATGGAGT

GTCACAATGTCACCTATCTCCTGCAACAAGAGCTGGCCGAGGCCCA

GCGGGGCTTTCGGGACGCAGAGGCCCAGGCTGTCACCTGCAACCAG

ACTGTG

SEQ ID NO: 10:
ATGGCACCTATTTTGTATGACTATTGCAAAATGCCCATGGATGACA

TTTGCAAGGAAGACAGGGACAAGTGCTGTAAACTGGCCGTAGGAAT

TCTGGGGCTCCTGGTCATAGTGCTTCTGGGGGTGCCCTGATTTTCT

TCATCATCAAGGCCAACAGCGAGGCCTGCCAGGATGGCCTCCGGGC

AGTGATGGAGTGTCACAATGTCACCTATCTCCTGCAACAAGAGCTG

GCCGAGGCCCAGCGGGGCTTTCGGGACGCAGAGGCCCAGGCTGTCA

CCTGCAACCAGACTGTG

The nucleotide sequences of the mutant cell lines produced in the present invention were analyzed, and as a result, it could be seen that a frameshift mutation in the alleles of the K-E4, J-C10 and J-D10 cell lines from MDCK cells occurred.

As used herein, the term "frameshift mutation" means a deletion or insertion of 1, 2 or more nucleotides (other than a multiple of 3) that result in a change in a frameshift that can read a genetic code of three nucleotides.

Among the mutant cell lines, J-D10 was deposited under the accession number KCLRF-BP-00285.

In another aspect, the present invention is directed to a method for preparing a virus-producing mutant cell line that is reduced from virus-induced apoptosis, the method comprising mutating Bst-2 gene in a virus-producing cell line.

In one example of the present invention, D-D8 and G-D5 cell lines were produced by deleting 1-12 nucleotides from the exon 1 region of the Bst-2 gene in the VERO cell line. It was shown that the apoptosis of the mutant cell lines upon infection with H1N1 or H3N2 virus was reduced.

The virus-producing mutant cell line reduced from virus-induced apoptosis according to the present invention may be an animal cell line.

The animal cell line may be any cell line that is used in the development of influenza vaccines. Preferably, it may be selected from the group consisting of MDCK, VERO and mouse fibroblasts.

The mutation according to the present invention may be an insertion, deletion, duplication, inversion, substitution or translocation of a portion of the exon 1 region of the Bst-2 gene, a deletion of the whole of the exon 1 region of the Bst-2 gene, or a silencing of the Bst-2 gene.

The exon 1 region of the Bst-2 gene may encode the cytoplasmic domain of Bst-2 protein.

In another example of the present invention, it was found that, when wild-type Bst-2 gene was introduced into Bst-deleted mouse fibroblasts, apoptosis similar to that of the wild-type cell line appeared, but when a Bst-2 gene having a deletion of the cytoplasmic domain was introduced, apoptosis was reduced, like that of the Bst-2-deleted cell line.

In another example of the present invention, it was shown that wild-type Vero cells underwent apoptosis after infection with influenza virus, and thus showed a low ability to produce virus, whereas Bst-2-mutated Vero cells were reduced from virus-induced apoptosis and showed an increase in virus production ability of 50 times or more after 3 days.

In still another example of the present invention, a Bst-2 gene having a deletion of the cytoplasmic domain involved in apoptosis was additionally expressed in normal mouse fibroblasts to interfere with the function of a normal gene. As a result, it was observed that the ability of the cells to produce virus. In addition, it was observed that, when the Bst-2 gene having a deletion of the cytoplasmic domain was expressed in a Bst-2-deleted B2K cell line having an increased ability to virus, the ability of the cells to produce virus was maintained. This demonstrates that an increase in the ability of the cells to produce virus is attributable to the reduction of apoptosis of the cells.

In still another aspect, the present invention is directed to a mutant cell line in which introduced a mutated Bst-2 gene in a virus-producing cell line that expresses no Bst-2, wherein the mutant cell line having an increased ability to produce virus by introducing the mutated Bst-2 gene.

The Bst-2-mutated gene may have an insertion, deletion, duplication, inversion, substitution or translocation of one or more nucleotides in a portion of the exon 1 region of wild-type Bst-2 gene, or a deletion of the whole of the exon 1 region wild-type Bst-2 gene, or a silencing of the Bst-2 gene.

In yet another aspect, the present invention is directed to a method for producing a desired virus, the method comprising the steps of: (a) infecting a mutant cell line, which has an increased ability to produce virus, with a desired virus; and (b) culturing the cell line infected with the desired virus, and then centrifuging the supernatant of the culture to recover the desired virus.

In the present invention, cells having a frameshift mutation were plated on a 6-well plate, cultured for 24-48 hours, and then inoculated into a medium containing influenza virus.

The number of the cells may be $1\times10^4$ to $1\times10^7$, preferably $5\times10^4$ to $5\times10^6$, and more preferably $1\times10^5$ to $1\times10^6$.

The virus inoculated into the medium is preferably infected in a 5% $CO_2$ incubator at 37° C. for 30 minutes to 2 hours.

The infected virus may be incubated in a fresh medium for 50-70 hours, and then the medium may be collected and centrifuged under suitable conditions to collect the supernatant. Preferably, the supernatant may be collected by performing centrifugation at 1500-5000 rpm at a temperature of 4° C. to 15° C. for 5-15 minutes.

In the present invention, a plaque that is formed upon viral infection of a mutant cell line expressing no Bst-2 gene was examined.

The mutant cell line was diluted in a medium and infected with virus, followed by culture. As a result, it could be seen that the ability of the mutant cell line to produce virus increased.

The mutant cell line having an increased ability to virus may be used for the production of a vaccine for preventing or treating a disease caused by influenza virus.

In a further aspect, the present invention is directed to a method for producing a vaccine against viral disease, the method comprising the steps of: (a) infecting a mutant cell line, which has an increased ability to produce virus, with a desired virus; (b) culturing the cell line infected with the desired virus, and then centrifuging the supernatant of the culture to recover the desired virus; and (c) attenuating or inactivating the recovered virus.

The vaccine composition may further comprise a pharmaceutically acceptable adjuvant or excipient. As the adjuvant, any adjuvant may be used, as long as it can promote antibody formation upon injection into the body to achieve the purpose of the present invention. Particularly, the adjuvant is preferably one or more selected from among aluminate ($Al(OH)_3$, $ALPO_4$), squalene, sorbitane, polysorbate 80, CpG, liposome, cholesterol, MPL (monophosphoryl lipid A) and GLA (glucopyranosyl lipid A), but is not limited thereto.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Production of Bst-2-Mutated MDCK Cell Line and Confirmation of Mutation Therein $5\times10^5$ wild-type MDCK cells obtained from the laboratory of Professor Moon-Jung Song (Korea University, Korea) were cultured in DMEM complete (GIBCO, USA) medium (containing 10% FBS, 2 mM L-glutamine, 5 μM β-mercaptoethanol, 10 μg/ml gentamicine, 50 U/ml penicillin, and 50 μg/ml streptomycin) in a 100Φ culture dish for 24 hours. Then, 15 μg of a mixture of a pair of TALEN vectors (ToolGen, Korea) capable of binding to the exon 1 region of the Bst-2 gene, represented by SEQ ID NO: 1, one reporter vector (ToolGen, Korea) and Turbofect reagent (Thermo, USA), was added to the cultured cells which were then incubated under the conditions of 37° C. and 5% $CO_2$ for 48 hours.

The cultured cells were sorted by FACS Aria (BD Bioscience, USA) to select 500 cells positive to both GFP and RFP, and the selected cells were seeded in a 96-well plate, thereby obtaining monoclonal cells.

In order to confirm a mutation in the obtained monoclonal cells, lysis buffer (50 mM Tris-Cl, pH8.0, 50 mM EDTA, 1% SDS, 10 mM NaCl, 100 μg/ml proteinase K) (300 μl) was added to the monoclonal cells which were then incubated at 54° C. for 16 hours. Then, 300 μl of a 1:1 mixture of phenol and chloroform was added to and mixed with the incubated cells, followed by centrifugation at 1700×g for 10 minutes. The supernatant (300 μl) was transferred into a fresh tube, and 100% ethanol (600 μl) and 3M sodium acetate (90 μl) were added thereto, followed by centrifugation at 1700×g for 10 minutes. Then, the supernatant was removed, 1 ml of 70% ethanol was added to the remaining material, followed by centrifugation at 1700×g for 2 minutes. Then, the supernatant was removed, and the genomic DNA remaining at the bottom was dried for 3 minutes, and then suspended in 50 μl of deionized water (DW). The extracted genomic DNA was subjected to polymerase chain reaction (PCR) using a dBst-2-F primer represented by SEQ ID NO: 11 and a dBst-2-R primer represented by SEQ ID NO: 12 under the following conditions: 95° C. for 5 min, and then 25 cycles, each consisting of 94° C. for 30 sec, 60° C. for 30 sec and 72° C. for 1 min, followed by 72° C. for 10 min.

The reaction product was diluted to $10^{-3}$, and subjected to PCR using an NdBst-2-F primer represented by SEQ ID NO: 13 and an NdBst-2-F primer represented by SEQ ID NO: 14 under the following conditions: 95° C. for 5 min, and then 25 cycles, each consisting of 94° C. for 30 sec, 60° C. for 30 sec and 72° C. for 1 min, followed by 72° C. for 10 min.

```
SEQ ID NO: 11:
GGTCAGGATGGCTCCTATGC

SEQ ID NO: 12:
AACCTGACAGGGTCACCTGG

SEQ ID NO: 13:
GTAGCCCCAGCCAAAGGTTTC

SEQ ID NO: 14:
AGGCCTCCCCATGCCCAAAC
```

In order to confirm a mutation in the target region of the reaction product, the reaction product was melted and annealed by PCR under the following conditions: keeping at 95° C. for 5 min, temperature lowering from 95° C. to 85° C. at a rate of 2° C./sec, temperature lowering from 85° C. to 25° C. at a rate of 0.3° C./sec, and stopping at 16° C. Then, the resulting reaction product was treated with T7E1 enzyme (ToolGen, Korea) and incubated at 37° C. for 15 minutes, after which the size of the reaction product was analyzed by electrophoresis. As a result, it was shown that the cell lines having a putative mutation in the exon 1 region represented by SEQ ID NO: 1 had a normal PCR reaction product size and two additional bands caused by cleavage with endonuclase, indicating that a mutation in the exon 1 region occurred (FIG. 1).

To analyze the nucleotide sequences of the cell lines confirmed to have a mutation, the PCR reaction product was digested with BglII-XbaI, ligated with a pUC18 vector, and cultured in a medium containing ampicillin and X-gal-IPTG, thereby obtaining white colonies. Among the obtained white colonies, 6 colonies were selected for each clone and sequenced.

As a result, it was shown that, among 7 mutant cell lines (K-E4, J-C10, J-D10, D-E2, K-G3, J-E2 and H-G5) having a deletion or insertion of nucleotides in the exon 1 region of Bst-2, 3 mutant cell lines (K-E4, J-C10, J-D10) had a frameshift mutation that occurred in a pair of alleles.

Example 2: Production of Bst-2-Mutated VERO Cell Line and Confirmation of Mutation Therein $5\times10^5$ wild-type VERO cells obtained from the laboratory of Chengyu Liang (University of Southern California) were cultured in DMEM complete (GIBCO, USA) medium (containing 10% FBS, 2 mM L-glutamine, 5 μM β-mercaptoethanol, 10 μg/ml gentamicine, 50 U/ml penicillin, and 50 μg/ml streptomycin) in a 100Φ culture dish for 24 hours. Then, 15 μg of a mixture of a pair of TALEN vectors (ToolGen, Korea) (L1-DAW and R1-RR) capable of binding to the exon 1 region of the Bst-2 gene, represented by SEQ ID NO: 1, one reporter vector (ToolGen, Korea) and Turbofect reagent (Thermo, USA), was added to the cultured cells which were then incubated under the conditions of 37° C. and 5% $CO_2$ for 48 hours.

The cultured cells were sorted by FACS Aria (BD Bioscience, USA) to select 500 cells positive to both GFP and RFP, and the selected cells were seeded in a 96-well plate, thereby obtaining monoclonal cells.

In order to confirm a mutation in the obtained monoclonal cells, lysis buffer (50 mM Tris-Cl, pH8.0, 50 mM EDTA, 1% SDS, 10 mM NaCl, 100 μg/ml proteinase K) (300 μl) was added to the monoclonal cells which were then incubated at 54° C. for 16 hours. Then, 300 μl of a 1:1 mixture of phenol and chloroform was added to and mixed with the incubated cells, followed by centrifugation at 1700×g for 10 minutes. The supernatant (300 μl) was transferred into a fresh tube, and 100% ethanol (600 μl) and 3M sodium acetate (90 μl) were added thereto, followed by centrifugation at 1700×g for 10 minutes. Then, the supernatant was removed, 1 ml of 70% ethanol was added to the remaining material, followed by centrifugation at 1700×g for 2 minutes. Then, the supernatant was removed, and the genomic DNA remaining at the bottom was dried for 3 minutes, and then suspended in 50 μl of deionized water (DW). The extracted genomic DNA was subjected to polymerase chain reaction (PCR) using a dBst-2-F primer represented by SEQ ID NO: 11 and a AGM-R primer represented by SEQ ID NO: 16 under the following conditions: 95° C. for 5 min, and then 25 cycles, each consisting of 94° C. for 30 sec, 60° C. for 30 sec and 72° C. for 1 min, followed by 72° C. for 10 min.

```
SEQ ID NO: 15:
GAGGGGGAGATCTGGATGG

SEQ ID NO: 16:
CTTCTCTGCATCCAGGGAAG
```

The reaction product was diluted with $10^{-3}$, and subjected to PCR using an AGM-F primer represented by SEQ ID NO: 15 and an AGM-R primer represented by SEQ ID NO: 16 under the following conditions: 95° C. for 5 min, and then 25 cycles, each consisting of 94° C. for 30 sec, 60° C. for 30 sec and 72° C. for 1 min, followed by 72° C. for 10 min.

Figure 2:
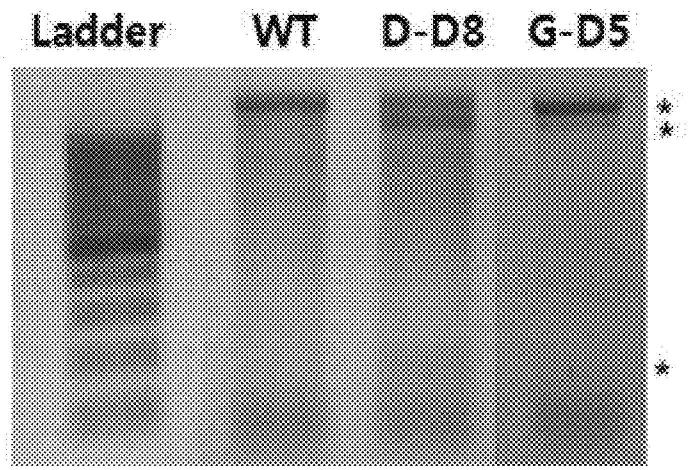
FIG. 2 shows the results of PCR products of VERO cell lines having a mutated Bst-2 gene by electrophoresis.

In order to confirm a mutation in the target region of the reaction product, the reaction product was melted and annealed by PCR under the following conditions: keeping at 95° C. for 3 min, temperature lowering from 85° C. to 25° C. at a rate of 2° C./sec, and stopping at 16° C. Then, the resulting reaction product was treated with T7E1 enzyme (ToolGen, Korea) and incubated at 37° C. for 15 minutes, after which the size of the reaction product was analyzed by electrophoresis. As a result, it was shown that two cell lines having a putative mutation in the exon 1 region of SEQ ID NO: 2 had a normal PCR reaction product size and two additional bands caused by cleavage with endonuclase, indicating that a mutation in the exon 1 region occurred (FIG. 2). Hereinafter, the single cell lines confirmed to have a mutation in Bst-2 were named "D-D8" and "G-D5".

Example 3: Ability of Bst-2-Mutated MDCK Cell Line to Produce Virus

In order to examine the virus production ability of the mutant cell line expressing no Bst-2 gene, the virus production ability of a wild-type MDCK cell line was compared with those of the cell lines K-E4, J-C10 and J-D10, which were obtained in Example 1 and had a frameshift mutation in the exon 1 region of the Bst-2 gene.

Specifically, each of the wild-type MDCK cell line and the mutant cell lines produced in Example 1 was seeded in a E-well plate at a density of $5\times10^4$ cells/well. After 48 hours, each of the cell lines was infected with 0.01 MOI of P/H1N1. After 72 hours, the supernatant was collected, and the titer of the supernatant was measured.

Figure 3:
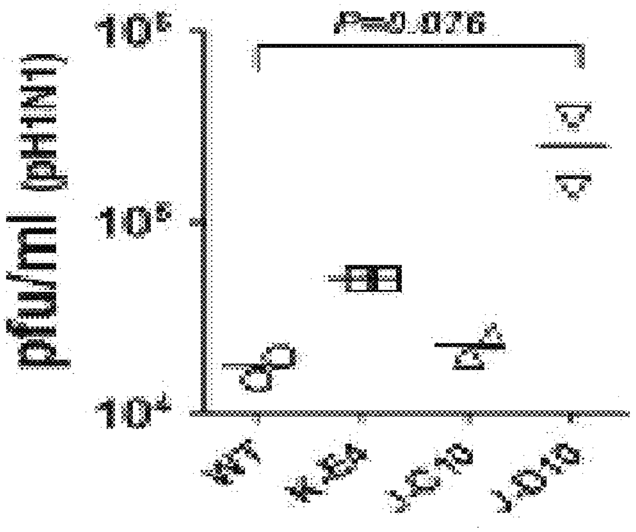
FIG. 3 shows the results of a plaque assay performed to measure the titers of the supernatants obtained after viral infection of wild-type MDCK cells and Bst-2-mutated MDCK cell lines.

As a result, as can be seen in FIG. 3, the virus production of K-E4 was $5\times10^4$ pfu/ml, which was three times higher than that of the wild-type MDCK cell line ($1.8\times10^4$ pfu/ml), and the virus production of J-C10 was $2.2\times10^4$ pfu/ml, which was 1.2 times higher than that of MDCK ($1.8\times10^4$ pfu/ml), and the virus production of J-D10 was $25\times10^4$ pfu/ml, which was 14 times higher than that of MDCK ($1.8\times10^4$ pfu/ml).

Figure 5:
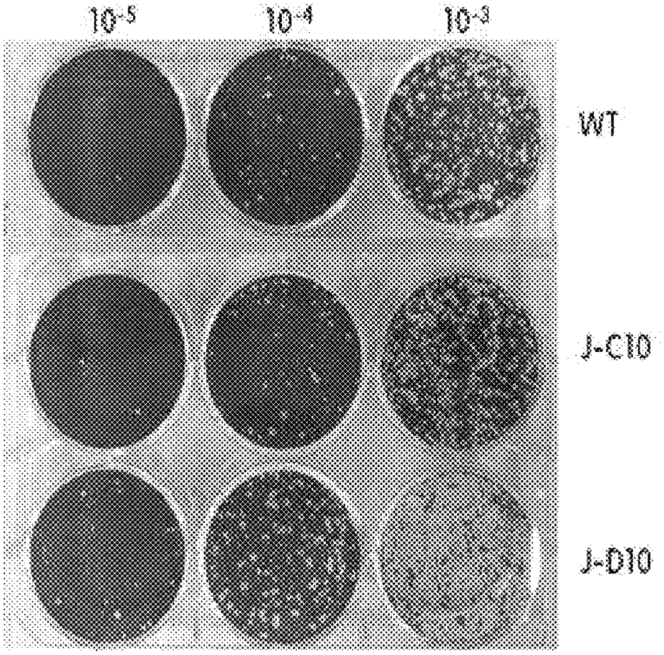
FIG. 5 shows the results obtained by diluting wild-type MDCK cells and Bst-2-mutated MDCK cell lines, infecting the diluted cells with virus and culturing the virus-infected cells.

In addition, each of the cell lines J-C10 and J-D10 was diluted to $10^{-3}$, $10^{-4}$ and $10^{-5}$ and infected with P/H1N1 virus, followed by incubation for 48 hours. As a result, as shown in FIG. 5, plaques formed by the virus were observed.

Thus, it could be seen that the mutant cell lines having a frameshift mutation silencing the Bst-2 gene had an increased ability to produce virus, compared to the wild-type cell line.

Example 4: Virus Production Ability of Bst-2-Mutated VERO Cell Line

In order to examine the virus production ability of the mutant cell line expressing no Bst-2 gene, the virus production ability of a wild-type VERO cell line was compared with those of the cell lines D-D8 and G-D5, which were obtained in Example 2 and had a mutation in the exon 1 region of the Bst-2 gene.

Specifically, each of the wild-type VERO cell line and the mutant cell lines produced in Example 2 was seeded in a 12-well plate at a density of $5\times10^5$ cells/well. After 24 hours, each of the cell lines was infected with 0.01 MOI of H3N2. After 60 hours, the supernatant was collected, and the titer of the supernatant was measured.

Figure 4:
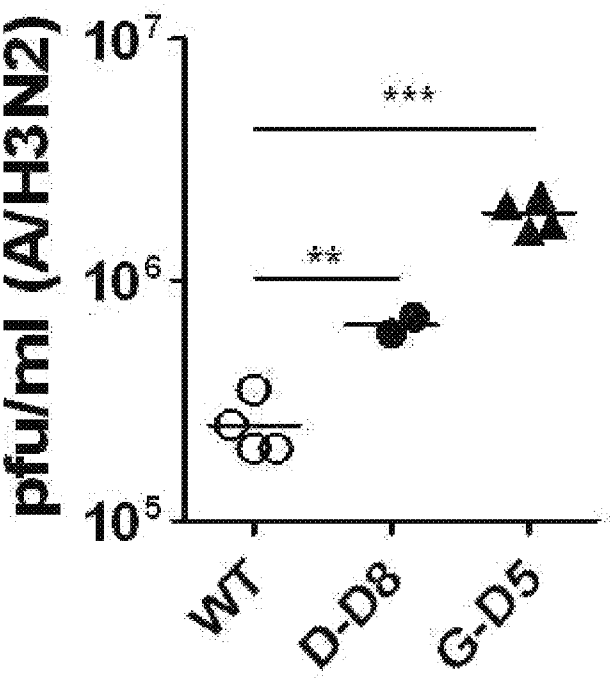
FIG. 4 shows the results of a plaque assay performed to measure the titers of the supernatants obtained after viral infection of wild-type VERO cells and Bst-2-mutated VERO cell lines.

As a result, as can be seen in FIG. 4, the virus productivity of D-D8 was $6.5\times10^5$ pfu/ml, which was three times higher than that of the wild-type VERO cell line ($2.5\times10^5$ pfu/ml), and the virus production of G-D5 was $1.9\times10^6$ pfu/ml, which was about 8 times higher than that of the wild-type VERO cell line ($2.5\times10^5$ pfu/ml).

Figure 6:
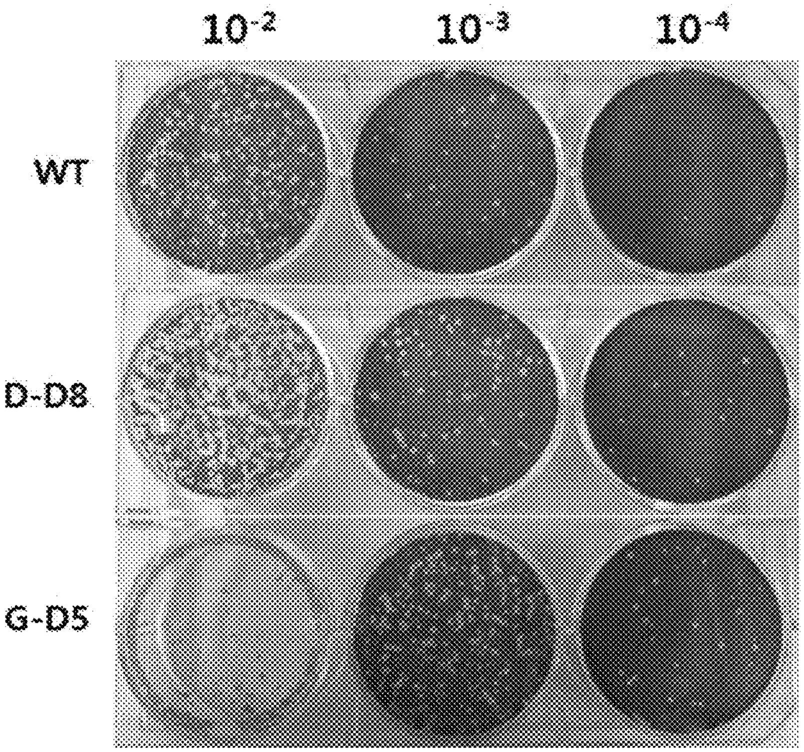
FIG. 6 shows the results obtained by diluting wild-type VERO cells and Bst-2-mutated VERO cell lines, infecting the diluted cells with virus and culturing the virus-infected cells.

In addition, each of the cell lines D-D8 and G-D5 was diluted to $10^{-3}$, $10^{-4}$ and $10^{-5}$ and infected with H3N2 virus, followed by incubation for 60 hours. As a result, as shown in FIG. 6, plaques formed by the virus were observed.

Thus, it could be seen that the mutant cell lines having a mutation silencing the Bst-2 gene had an increased ability to produce virus, compared to the wild-type cell line.

Example 5: Effect of Bst-2 on Intracellular Signaling

Figure 7:
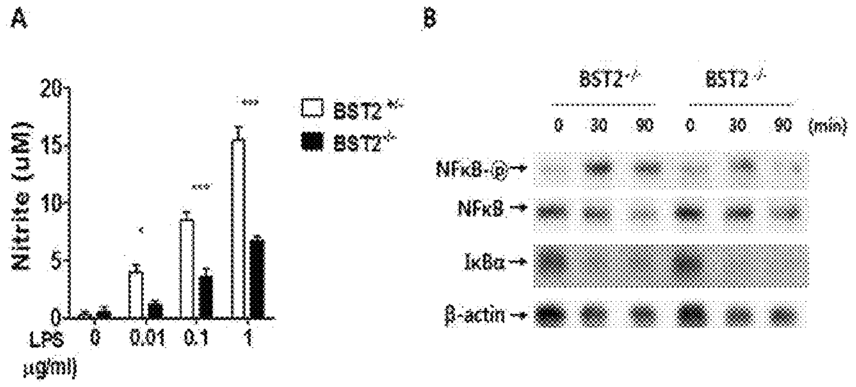
FIG. 7 shows that intercellular signaling in Bst-2-deleted cells decreases. (A: comparison of nitrite production by treatment with varying concentrations of LPS; and B: comparison of phosphorylation of NFκB by treatment with LPS).

Bst-2 knockout mice (ISU Abxis, Korea) were mated with wild-type B6 mice (Orient Bio, Korea) to generate Bst-2 hetero mice. From the abdominal cavity of the Bst-2 hetero mice and the knockout mice, macrophages were obtained. Among the obtained cells, $1\times10^6$ cells were added to each well of a 96-well flat bottom plate and treated with 0, 0.01, 0.1 and 1 μg/ml of LPS (lipopolysaccharide), followed by culture for 24 hours. The concentration of nitrite in the culture medium was measured using a Griess technique. As a result, the macrophages obtained from the Bst-2 knockout mice showed a decrease in nitrite production of about 60% compared to that shown by the macrophages obtained from the Bst-2 hetero mice (FIG. 7A).

Macrophages were obtained from the Bst-2 hetero mice and knockout mice. Among the obtained cells, $5\times10^6$ cells were seeded in each well of a 6-well plate and allowed to stand for 2 hours to adhere to the culture dish. Then, the cells were treated with 100 ng/ml of LPS. After 30 minutes and 90 minutes, protein was obtained from the cells using M-PER buffer (Pierce Biotechnology, USA). For each sample, 30 μg of total protein was separated according to size by SDS-PAGE electrophoresis and attached to a PVDF membrane. Anti-phosphorylation-NFκB antibody (clone 93H1), anti-NFκB antibody (clone C22B4) and anti-IκBα antibody (clone L35A5) used were purchased from Cell Signaling Technology (USA), and secondary antibody used was purchased from HRP-conjugated anti-rabbit IgG (Koma Biotech, Korea). After the antibody reactions, the signals were developed with ECL plus or ELC fempto (Pierce Biotechnology, USA), and then imaged with LAS 3000. As a result, it was shown that the ratio of phosphorylated NF-κB to total NF-κB decreased by about 90% (FIG. 7B). Thus, it was observed that, when Bst-2 was mutated, intracellular signal was reduced.

Example 6: Delay of Apoptosis of Bst-2-Deleted Cell Line 6-1: Observation of Apoptosis of Cell Line Infected with Virus Each of a wild-type (WT) Vero cell line, a Bst-2 hetero (D-D8) Vero cell line and a Bst-2 knockout (G-D5) cell line was added to each well of a 6-well plate at a density of $1\times10^6$ cells. After 20 hours, the cells were infected with 0.1 MOI of each of seasonal H1N1 influenza (FIG. 8A) or H3N2 influenza (FIG. 8B).

Figure 8:
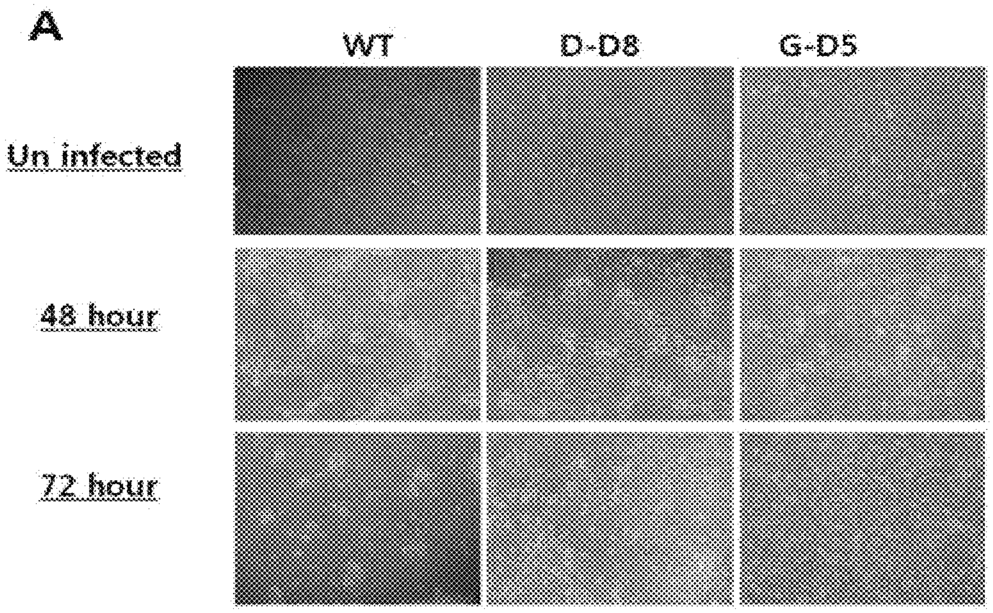
FIG. 8 is a set of photographs showing that the pattern of apoptosis in Bst-2-deleted cells after viral infection apparently decreases. (A: Vero cell line infected with H1N1; and B: Vero cell line infected with H3N2).
Figure 8:
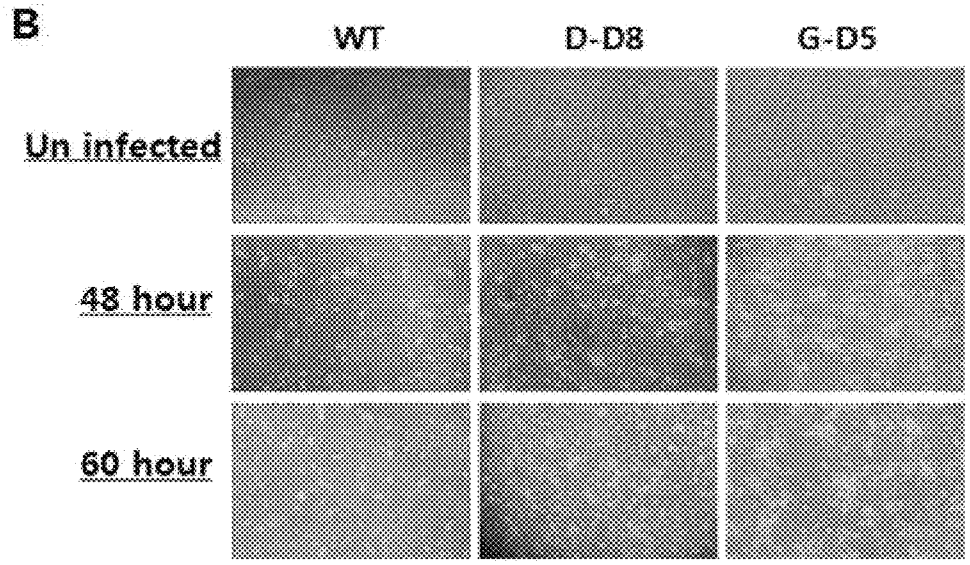

At 48 hours and 72 hours after infection, the shape of the modified cells was analyzed. As a result, normal cells were mostly dead at 1 day or 2 days after infection with the virus, but in the case of the Bst-2-deleted cells, a significant number of the cells maintained the normal cell shape even at day 2 after viral infection. Specifically, the wild-type cells showed a typical apoptotic shape with the cell membrane distorted, whereas the Bst-2 knockout cells (G-D5) mostly maintained the normal cell shape at 48 hours and hours (FIG. 8). The Bst-2 hetero cells (D-D8) showed apoptosis at a level intermediate between the wild-type cells and the knockout cells.

6-2: Observation of Expression of Phosphatidylserine in Cell Lines Infected with Virus As apoptosis progresses, phosphatidylserine (PS) present in the inner cell membrane migrates to the outer cell membrane, and thus can be detected by staining. Thus, in order to compare the degree of apoptosis, cells were stained with annexin-V that recognizes the indicator PS.

Specifically, each of a wild-type (WT) Vero cell line, a Bst-2 hetero (D-D8) Vero cell line and a Bst-2 knockout (G-D5) cell line was attached to each well of a 6-well plate at a density of $1\times10^6$ cells. After 20 hours, each of the cell lines was infected with 0.1 MOI of seasonal H1N1 or H3N2 influenza. At 48 hours or 72 hours after infection, the cells were detached, and PBS was added thereto, and the cell solution was centrifuged at 1250 rpm at room temperature for minutes to remove the supernatant. Then, a buffer containing Annexin V-FITC (BD Biosciences, USA) and Annexin V was added to the cells which were then stained in a dark place for 15 minutes.

Figure 9:
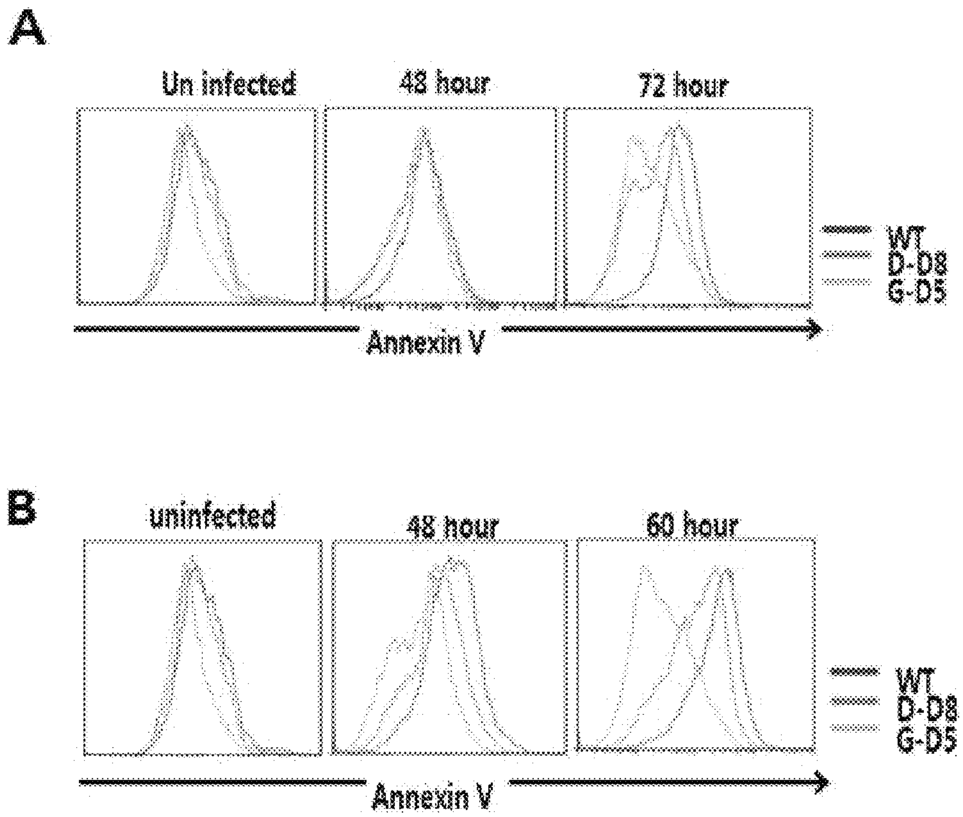
FIG. 9 shows the results of performing phosphatidylserine (apoptosis indicator) staining to observe a phenomenon in which the pattern of apoptosis in Bst-2-deleted cells after viral infection apparently decreases. (A: Vero cell line infected with H1N1; and B: Vero cell line infected with H3N2).

As a result, it was observed that the wild-type cells strongly expressed PS on the cell surface at 72 hours after infection with H1N1 virus, whereas the knockout cell line (G-D5) still maintained a low level of the expression of PS (FIG. 9A). The Bst-2 hetero cell line (D-D8) expressed PS at a level intermediate between the wild-type cell line and the knockout cell line.

Meanwhile, it was observed that the same patterns also appeared when the cells were infected with H3N2 virus (FIG. 9B). Specifically, as the expression level of the Bst-2 gene decreased the expression of Annexin V indicating the progression of apoptosis also decreased.

6-3: Increase in Apoptosis of Bst-2-Reintroduced Cell Line

To produce a mouse fibroblast cell line (B2K) lacking Bst-2, 100 μg of MCA (3-methyl cholanthrene) was injected into the thigh of 24-week-old Bst-2 knockout mice (ISU Abxis, Korea). After about 4 months, a tumor formed in the thigh was detached and washed with 70% ethanol to remove bacteria, after which it transferred into a dish containing 10% FBS and RPMI medium and was cut into fine pieces using surgical scissors. The tumor pieces and 13 ml of digestion solution (500 unit/ml collagenase IV, 150 Unti/ml DNase I) were placed in a 50-ml conical tube and shaken in a shaker at 250 rpm 37° C. for 1 hour and 30 minutes. The shaken solution was pipetted 3-5 times with a 10-ml pipette to further disperse the pieces, and then filtered through a nylon mesh and placed in a 50-ml fresh conical tube. Then, the resulting solution was centrifuged at 1250 rpm for 5 minutes, and the supernatant was removed, after which the pellets were suspended in a fresh medium, filtered through a nylon mesh, and centrifuged under the above-described conditions. After removal of the supernatant, the pellets were dissociated, seeded at a density of $2.4\times10^7$ cells per 10 cm dish, and cultured to obtain a knockout tumor cell line (B2K).

Meanwhile, to produce a wild-type tumor cell line (MB19), 100 μg of MCA (3-methyl cholanthrene) was injected into the thigh of 24-week-old B6 wild-type mice (Orient Bio, Korea). After about 4 months, a tumor formed in the thigh was detached and washed with 70% ethanol to remove bacteria, after which it transferred into a dish containing 10% FBS and RPMI medium and was cut into fine pieces using surgical scissors. The tumor pieces and 13 ml of digestion solution (500 unit/ml collagenase IV, 150 Unti/ml DNase I) were placed in a 50-ml conical tube and shaken in a shaker at 250 rpm 37° C. for 1 hour and 30 minutes. The shaken solution was pipetted 3-5 times with a 10-ml pipette to further disperse the pieces, and then filtered through a nylon mesh and placed in a 50-ml fresh conical tube. Then, the resulting solution was centrifuged at 1250 rpm for 5 minutes, and the supernatant was removed, after which the pellets were suspended in a fresh medium, filtered through a nylon mesh, and centrifuged under the above-described conditions. After removal of the supernatant, the pellets were dissociated, seeded at a density of $2.4\times10^7$ cells per 10 cm dish, and cultured to obtain a wild-type tumor cell line (MB19).

The MHC class (KbDb(R1.21.2)-APC, CD1d(1B1)-PE), LFA-1(207)-Cyc and Bst-2(e.Bio927)biotin+Streptavidin-PE of each of the Bst-2 knockout cell line (B2K) and the Bst-2 wild-type tumor cell line (MB19) were fluorescence-stained, and the expression levels thereof were compared. Specifically, B2K cells and MB19 cells were suspended in 50 μl of FACS buffer at a density of $1\times10^6$ cells, and 20 μg/ml of 2.4G2 antibody was added to the cells which were then incubated on ice for 20 minutes to block the Fcγ receptor on the cell surface. Then, Bst-2 biotin (1 μg/ml) was added to the cells which were then incubated on ice for 30 minutes. Next, 500 μl of FACS buffer was added to the cells, and the cell solution was centrifuged at 1250 rpm at 4° C. for 4 minutes, and the supernatant was removed to remove the remaining antibody. In addition, another antibody, KbDb-APC (0.1 μg/ml), CD1d-PE (1.5 μg/ml), LFA-1 (1 μg/ml) or Streptavidin-PE (0.5 μg/ml), was added to the cells which were then incubated on ice under a light-shielded condition. After 30 minutes, in order to remove the remaining antibody, 500 μl of FACS buffer was added to the cells, and the cell solution was centrifuged at 1250 rpm at 4° C. for 4 minutes. Analysis was performed using FACS caliber (Becton Dickinson, Germany). As a result, it was observed that MB19 normally expressed Bst-2, whereas the B2K tumor cell line did not express Bst-2. Thus, the B2K tumor cell line was used in the following Example.

Into the established B2K cells (B2K empty), a Bst-2 wild-type gene (Flag WT; SEQ ID NO: 17), a gene (Flag ΔCT: SEQ ID NO: 18) having a deletion of the cytoplasmic domain, or an empty vector was introduced.

```
SEQ ID NO: 17:
ATGGCGCCCTCTTTCTATCACTATCTGCCCGTGCCCATGGATGAGA

TGGGGGGGAAGCAAGGATGGGGCAGCCACCGGCAGTGGCTGGGGTA

CCGCGGGAGAAAGATAGTGATAGACGGGAACGGGTACCTACTCTAC

CCCCCCTTCGTTCCTACCCCGTCGGTGGCCGTCACCGACCCC

SEQ ID NO: 18:
ATGTACCGCGGGAGAAAGATAGTGATAGACGGGAACGGGTACCTAC

TCTACCCCCCCTTCGTTCCTACCCCGTCGGTGGCCGTCACCGACCC

C
```

Figure 10:
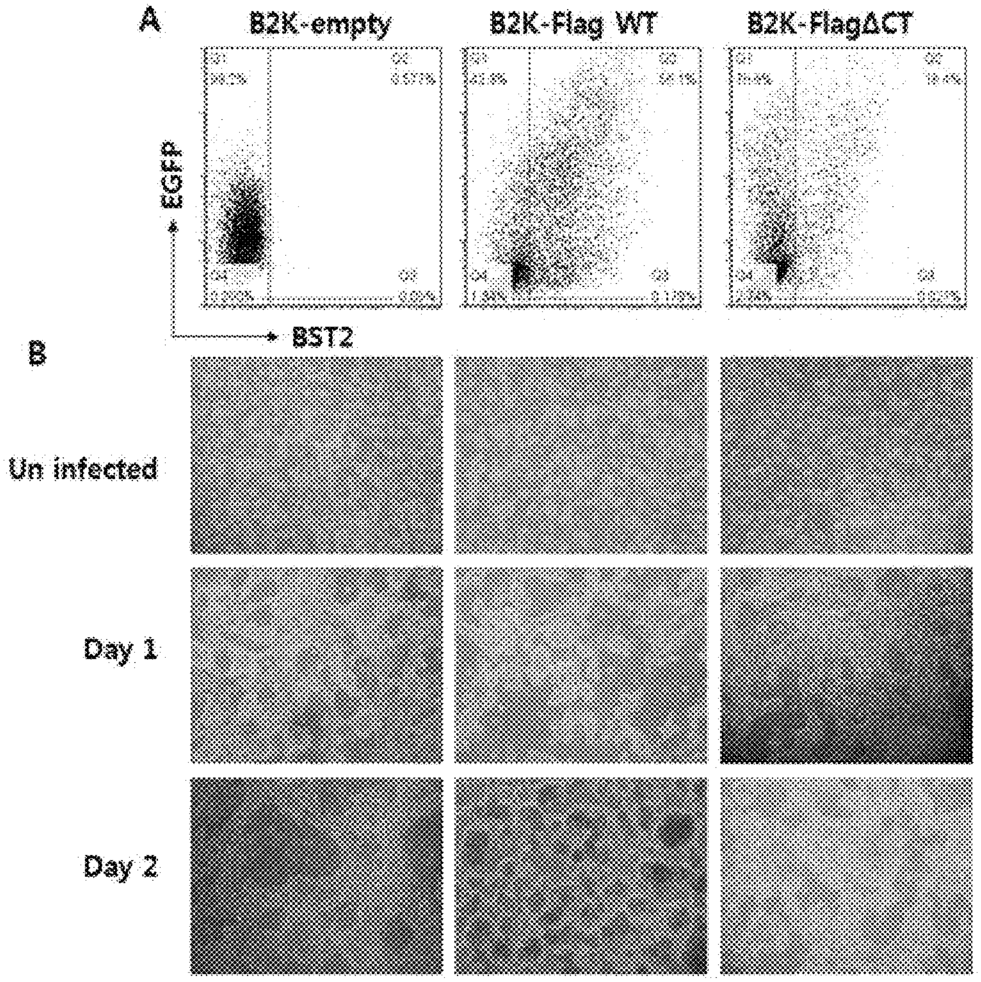
FIG. 10 shows the results of a Bst-2 reintroduction experiment performed to demonstrate that the cytoplasmic domain is involved in apoptosis. (A: FACS analysis of Bst-2 expression after reintroduction of Bst-2; and B: comparison of apoptosis after infection with MHV68 virus).

These genes had the Flag or V5 protein attached to the N-terminus, and the expression thereof was analyzed using anti-Bst-2 antibody (PDCA-1, eBio927: Ebioscience, USA) (FIG. 10A). The results of FACS analysis indicated that the B2K empty did not express Bst-2 protein due to the inhibition of Bst-2, and thus no dot appeared in the Q2 region and Q3 region. In the case of Flag WT comprising the Bst-2 wild-type gene introduced into the B2K empty, 56% or more of the cells were present in the Q2 and Q3 region.

Each of the B2K empty, B2K-Flag WT and B2K-Flag V5 ΔCT cell lines was added to each of a 6-well plate at a density of $2\times10^6$ cells. After 20 hours, each of the cell lines was infected with 0.1 MOI of MHV-68 virus. After 1 day (24 hours) or 2 days (48 hours), the cell shape was photographed. As a result, as shown in FIG. 10B, it was observed that, in the case of the cells (B2K-Flag WT) reintroduced with the wild-type Bst-2 gene, apoptosis was induced quickly, whereas, in the case of the cells (B2K-FlagV5 ΔCT) introduced with the Bst-2 gene having a deletion of the cytoplasmic domain determined to be involved in signaling, apoptosis was still delayed.

In other words, through the Bst-2 reintroduction experiment, it was first demonstrated that the cytoplasmic domain plays an important role in signaling that induces the apoptosis of virus-infected cells. This fact indicates that, when the survival time of cells infected with any virus is extended, the production of the virus can be continued and the amount of virus produced can be increased.

6-4: Increase in Virus Production Ability of Bst-2-Mutated Cell Line

In order to examine the virus production ability of the Bst-2 mutant cell line reduced from virus-induced apoptosis, the virus production ability of the wild-type VERO cell line was compared with those of the cell lines D-D8 and G-D5, which were produced in Example 2 and have a mutation in the exon 1 region of the Bst-2 gene.

Specifically, each of the VERO wild-type cell line and the mutant cell line produced in Example 2 was seeded in a 6-well plate at a density of $1\times10^6$ cells/well. After 24 hours, each of the cell lines was infected with 0.1 MOI of H3N2. After 48, 60 or 72 hours, the supernatant was collected, and the titer of the supernatant was measured.

Figure 11:
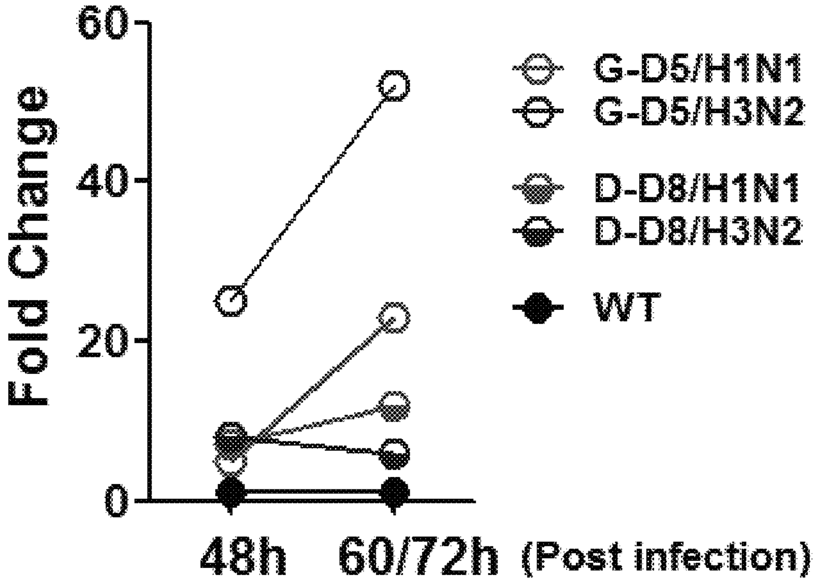
FIG. 11 shows that the virus production ability of Bst-2-mutated Vero cell lines significantly increases due to a decrease in the apoptosis thereof.

As a result, as shown in FIG. 11, it was observed that the wild-type cell line showed a low titer in the medium due to apoptosis after infection with influenza virus, whereas the mutant cell line showed 50 times higher virus production ability up to 72 hours due to the reduction of virus-induced apoptosis thereof. This effect was better in the G-D5 cells than the G-D8 cells.

Figure 12:
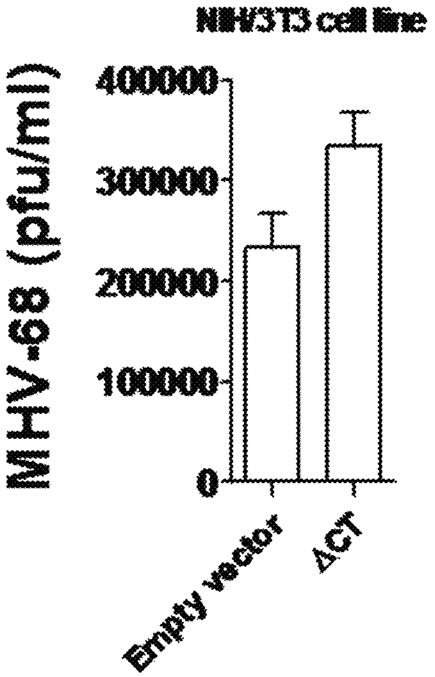
FIG. 12 shows that the production of virus increases when Bst-2 having a deletion of the cytoplasmic domain is additionally expressed in a normal NIH/3T3 cell line.
Figure 13:
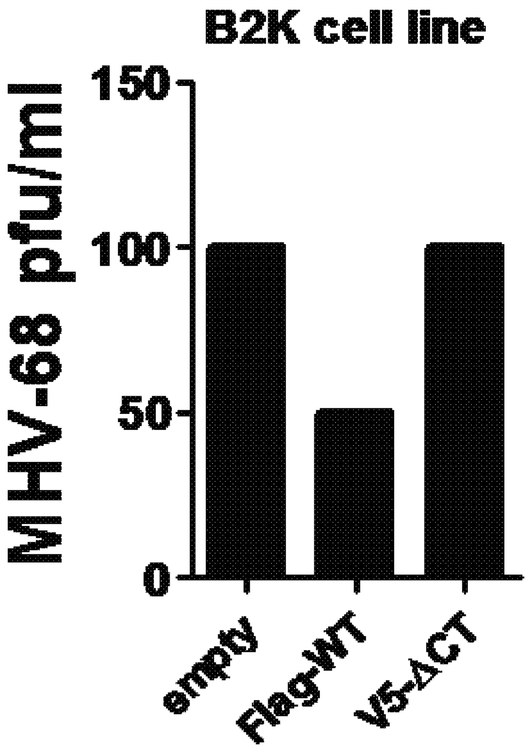
FIG. 13 shows the results of an experiment performed using B2K to demonstrate that an increase in the virus production of a Bst-2-deleted cell line is attributable to the inhibition of apoptosis.

6-5: Increase in the Ability of Bst-2-Mutated Cell Line to Produce Herpes Simplex Virus In the same manner as described in Example 6-3, the Bst-2 gene having a deletion of the cytoplasmic domain was introduced (ΔCT) into fibroblasts (NIH/3T3) that normally express Bst-2. An empty vector containing no Bst-2 was introduced into control normal cells, and the virus production ability of the control cells was compared with that of the mutant cell line. As a result, as can be seen in FIG. 12, it could be observed that the virus production ability of the mutant cell line lacking the normal function of the Bst-2 gene due to the introduction of the Bst-2 mutant gene increased by about 1.5 times.

In order to reproduce the same effect in other cell lines, according to the same method as described in Example 6-3, B2K cells were infected with Herpes simplex virus, and the virus production ability thereof was compared. As a result, the Bst-2-deleted B2K cells (empty) showed an increased ability to produce virus, whereas the virus production ability of the B2K cells (Flag-WT) reintroduced with the wild-type Bst-2 gene decreased by about 50%, and was similar to that of the wild-type cells. Meanwhile, the B2K cells (V5-ΔCT) reintroduced with the wild-type Bst-2 gene having a deletion of the cytoplasmic domain showed no decrease in the virus production ability. This demonstrates that the reduction of virus-induced apoptosis is very important to increase the virus production ability of cells. In addition, it was proven that the cell line of the present invention, which has an increased ability to produce virus, is useful not only for the production of influenza virus as described in the examples above, but also for the production of other infectious viruses.

INDUSTRIAL APPLICABILITY

As described above, according to the present invention, a cell line lacking the function of the Bst-2 gene has an excellent ability to produce virus, compared to a wild-type cell line. Thus, when the mutant cell line is used as a virus-producing cell line, the production yield of virus can be increased. In addition, the mutant cell line can be used for the production and research of vaccines for preventing and treating viral diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for preparing a virus-producing mutant cell line, the method comprising mutating a Bst-2 gene to lack the function of the Bst-2 gene in a virus-producing cell line.

2. The method of claim 1, wherein the virus-producing mutant cell line is an animal cell line.

3. The method of claim 2, wherein the animal cell line is selected from the group consisting of MDCK, VERO and mouse fibroblasts.

4. The method of claim 1, wherein the virus is influenza virus.

5. The method of claim 1, wherein the virus is Herpes simplex virus.

6. The method of claim 4, wherein the influenza virus is selected from the group consisting of Pandemic/H1N1, A/H1N1, and A/H3N2.

7. The method of claim 1, wherein the mutation is an insertion, deletion, duplication, inversion, substitution or translocation of a portion of the exon 1 region of the Bst-2 gene, a deletion of the whole of the exon 1 region of the Bst-2 gene, or a silencing of the Bst-2 gene.

8. The method of claim 7, wherein the exon 1 region of the Bst-2 gene encodes the cytoplasmic domain of Bst-2 protein.

9. A virus-producing mutant cell line which lacked the function of Bst-2 gene in a cell line having an ability to produce virus, wherein the mutant cell line having an increased ability to produce virus by lacking the function of said Bst-2 gene.

10. The virus-producing mutant cell line of claim 9, wherein the mutant cell line has an insertion, deletion, duplication, inversion, substitution or translocation of a portion of the Bst-2 gene, a deletion of the whole of the Bst-2 gene, or a silencing of the Bst-2 gene.

11. The virus-producing mutant cell line of claim 10, wherein the mutant cell line has a deletion of 1-15 nucleotides from the exon 1 region of the Bst-2 gene or an insertion of 1-15 nucleotides in the exon 1 region.

12. The virus-producing mutant cell line of claim 11, wherein the mutant cell line has a deletion of 1-4 nucleotides from positions 45 to 50 of the exon 1 region of the Bst-2 gene or an insertion of 1-3 nucleotides in positions 45 to 50 of the exon 1 region.

13. The virus-producing mutant cell line of claim 11, wherein the mutant cell line has a deletion of 1-12 nucleotides from positions 116 to 130 of the exon 1 region of the Bst-2 gene.

14. The virus-producing mutant cell line of claim 11, wherein the mutant cell line has a deletion of nucleotides from positions 4 to 90 of the exon 1 region of the Bst-2 gene.

15. A virus-producing mutant cell line in which introduced a mutated Bst-2 gene in a virus-producing cell line that expresses no Bst-2, wherein the mutant cell line having an increased ability to produce virus by introducing the mutated Bst-2 gene.

16. The virus-producing mutant cell line of claim 15, wherein the Bst-2-mutated gene has an insertion, deletion, duplication, inversion, substitution or translocation of a portion of the exon 1 region of wild-type Bst-2 gene, a deletion of the whole of the exon 1 region of wild-type Bst-2 gene, or a silencing of the Bst-2 gene.

17. A method for producing a desired virus, the method comprising the steps of:

(a) infecting the mutant cell line having an increased ability to produce virus of claim 9 with a desired virus; and (b) culturing the cell line infected with the desired virus, and then centrifuging the supernatant of the culture to recover the desired virus.

18. The method of claim 17, wherein the cell line is infected with 0.005-0.05 MOI of the desired virus.

19. A method for producing a vaccine against viral disease, the method comprising the steps of:

(a) infecting the mutant cell line having an increased ability to produce virus of claim 9 with a desired virus;

(b) culturing the cell line infected with the desired virus, and then centrifuging the supernatant of the culture to recover the desired virus; and (c) attenuating or inactivating the recovered virus.

20. A method for producing a desired virus, the method comprising the steps of:

(a) infecting the mutant cell line having an increased ability to produce virus of claim 15 with a desired virus; and (b) culturing the cell line infected with the desired virus, and then centrifuging the supernatant of the culture to recover the desired virus.

21. A method for producing a vaccine against viral disease, the method comprising the steps of:

(a) infecting the mutant cell line having an increased ability to produce virus of claim 15 with a desired virus;

(b) culturing the cell line infected with the desired virus, and then centrifuging the supernatant of the culture to recover the desired virus; and (c) attenuating or inactivating the recovered virus.

* * * * *

UNITED STATES PATENT AND TRADEMARK OFFICE

CERTIFICATE OF CORRECTION

PATENT NO. : 9,650,613 B2
APPLICATION NO. : 14/773741
DATED : May 16, 2017
INVENTOR(S) : Se-Ho Park et al.

It is certified that error appears in the above-identified patent and that said Letters Patent is hereby corrected as shown below:

In the Specification

Column 2, Line 60: "techniques (fang J. et al., Appl.," should be --techniques (Jang J. et al., Appl.--.

Column 13, Line 30: "a E-well plate" should be --a 6-well plate--.

Signed and Sealed this
Twentieth Day of June, 2017

Joseph Matal

*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 18

<210> SEQ ID NO 1
<211> LENGTH: 306
<212> TYPE: DNA
<213> ORGANISM: Artificial Sequence
<220> FEATURE:
<223> OTHER INFORMATION: Bst-2 mutant 1

<400> SEQUENCE: 1

atggcaccta cgctttacca ctactactgg cctgtgccca taactgacga gtcagagtca      60

atgtcatcaa gtcagaagct gagctggctg gagtggctgg gcatcttggg gatcccagtg     120

gtgatgggtc tgtctgtggc tctgatcatc tttgttgtca agaccaacag caaagcctgc     180

ggggatggcc tcctagtaga gcaggagtgt cacaatgtca ccagcctcct ggagcgccaa     240

ctaacccaaa cccggcaagc gttacagggg accatggacc aggctaccac ctgcaacaag     300
```

-continued

```
actgtg                                                                306

<210> SEQ ID NO 2
<211> LENGTH: 294
<212> TYPE: DNA
<213> ORGANISM: Artificial Sequence
<220> FEATURE:
<223> OTHER INFORMATION: Bst-2 mutant 2

<400> SEQUENCE: 2

atggcaccta ttttgtatga ctattgcaaa atgcccatgg atgacatttg caaggaagac     60

agggacaagt gctgtaaact ggccgtagga attctggggc tcctggtcat agtgcttctg    120

ggggtgcccc tgattttctt catcatcaag gccaacagcg aggcctgcca ggatggcctc    180

cgggcagtga tggagtgtca caatgtcacc tatctcctgc aacaagagct ggccgaggcc    240

cagcggggct ttcgggacgc agaggcccag gctgtcacct gcaaccagac tgtg          294

<210> SEQ ID NO 3
<211> LENGTH: 304
<212> TYPE: DNA
<213> ORGANISM: Artificial Sequence
<220> FEATURE:
<223> OTHER INFORMATION: Bst-2 mutant 3

<400> SEQUENCE: 3

atggcaccta cgctttacca ctactactgg cctgtgccca taactgaagt cagagtcaat     60

gtcatcaagt cagaagctga gctggctgga gtggctgggc atcttgggga tcccagtggt    120

gatgggtctg tctgtggctc tgatcatctt tgttgtcaag accaacagca aagcctgcgg    180

ggatggcctc ctagtagagc aggagtgtca caatgtcacc agcctcctgg agcgccaact    240

aacccaaacc cggcaagcgt tacaggggac catggaccag gctaccacct gcaacaagac    300

tgtg                                                                  304

<210> SEQ ID NO 4
<211> LENGTH: 304
<212> TYPE: DNA
<213> ORGANISM: Artificial Sequence
<220> FEATURE:
<223> OTHER INFORMATION: Bst-2 mutant 4

<400> SEQUENCE: 4

atggcaccta cgctttacca ctactactgg cctgtgccca taacacgagt cagagtcaat     60

gtcatcaagt cagaagctga gctggctgga gtggctgggc atcttgggga tcccagtggt    120

gatgggtctg tctgtggctc tgatcatctt tgttgtcaag accaacagca aagcctgcgg    180

ggatggcctc ctagtagagc aggagtgtca caatgtcacc agcctcctgg agcgccaact    240

aacccaaacc cggcaagcgt tacaggggac catggaccag gctaccacct gcaacaagac    300

tgtg                                                                  304

<210> SEQ ID NO 5
<211> LENGTH: 302
<212> TYPE: DNA
<213> ORGANISM: Artificial Sequence
<220> FEATURE:
<223> OTHER INFORMATION: Bst-2 mutant 5

<400> SEQUENCE: 5

atggcaccta cgctttacca ctactactgg cctgtgccca taactagtca gagtcaatgt     60
```

-continued

```
catcaagtca gaagctgagc tggctggagt ggctgggcat cttggggatc ccagtggtga    120

tgggtctgtc tgtggctctg atcatctttg ttgtcaagac caacagcaaa gcctgcgggg    180

atggcctcct agtagagcag gagtgtcaca atgtcaccag cctcctggag cgccaactaa    240

cccaaacccg gcaagcgtta caggggacca tggaccaggc taccacctgc aacaagactg    300

tg                                                                   302


<210> SEQ ID NO 6
<211> LENGTH: 303
<212> TYPE: DNA
<213> ORGANISM: Artificial Sequence
<220> FEATURE:
<223> OTHER INFORMATION: Bst-2 mutant 6

<400> SEQUENCE: 6

atggcaccta cgctttacca ctactactgg cctgtgccca taactgagtc agagtcaatg     60

tcatcaagtc agaagctgag ctggctggag tggctgggca tcttggggat cccagtggtg    120

atgggtctgt ctgtggctct gatcatcttt gttgtcaaga ccaacagcaa agcctgcggg    180

gatggcctcc tagtagagca ggagtgtcac aatgtcacca gcctcctgga gcgccaacta    240

acccaaaccc ggcaagcgtt acaggggacc atggaccagg ctaccacctg caacaagact    300

gtg                                                                  303


<210> SEQ ID NO 7
<211> LENGTH: 302
<212> TYPE: DNA
<213> ORGANISM: Artificial Sequence
<220> FEATURE:
<223> OTHER INFORMATION: Bst-2 mutant 7

<400> SEQUENCE: 7

atggcaccta cgctttacca ctactactgg cctgtgccca taacgagtca gagtcaatgt     60

catcaagtca gaagctgagc tggctggagt ggctgggcat cttggggatc ccagtggtga    120

tgggtctgtc tgtggctctg atcatctttg ttgtcaagac caacagcaaa gcctgcgggg    180

atggcctcct agtagagcag gagtgtcaca atgtcaccag cctcctggag cgccaactaa    240

cccaaacccg gcaagcgtta caggggacca tggaccaggc taccacctgc aacaagactg    300

tg                                                                   302


<210> SEQ ID NO 8
<211> LENGTH: 309
<212> TYPE: DNA
<213> ORGANISM: Artificial Sequence
<220> FEATURE:
<223> OTHER INFORMATION: Bst-2 mutant 8

<400> SEQUENCE: 8

atggcaccta cgctttacca ctactactgg cctgtgccca taactgacga cgagtcagag     60

tcaatgtcat caagtcagaa gctgagctgg ctggagtggc tgggcatctt ggggatccca    120

gtggtgatgg gtctgtctgt ggctctgatc atctttgttg tcaagaccaa cagcaaagcc    180

tgcggggatg gcctcctagt agagcaggag tgtcacaatg tcaccagcct cctggagcgc    240

caactaaccc aaacccggca agcgttacag gggaccatgg accaggctac cacctgcaac    300

aagactgtg                                                            309


<210> SEQ ID NO 9
<211> LENGTH: 282
```

-continued

<212> TYPE: DNA
<213> ORGANISM: Artificial Sequence
<220> FEATURE:
<223> OTHER INFORMATION: Bst-2 mutant 9

<400> SEQUENCE: 9
atggcaccta ttttgtatga ctattgcaaa atgcccatgg atgacatttg caaggaagac 60
agggacaagt gctgtaaact ggccgtagga attctggggc tcctggtcat agtgcccctg 120
attttcttca tcatcaaggc caacagcgag gcctgccagg atggcctccg ggcagtgatg 180
gagtgtcaca atgtcaccta tctcctgcaa caagagctgg ccgaggccca gcggggcttt 240
cgggacgcag aggcccaggc tgtcacctgc aaccagactg tg 282

<210> SEQ ID NO 10
<211> LENGTH: 293
<212> TYPE: DNA
<213> ORGANISM: Artificial Sequence
<220> FEATURE:
<223> OTHER INFORMATION: Bst-2 mutant 10

<400> SEQUENCE: 10
atggcaccta ttttgtatga ctattgcaaa atgcccatgg atgacatttg caaggaagac 60
agggacaagt gctgtaaact ggccgtagga attctggggc tcctggtcat agtgcttctg 120
ggggtgccct gattttcttc atcatcaagg ccaacagcga ggcctgccag gatggcctcc 180
gggcagtgat ggagtgtcac aatgtcacct atctcctgca acaagagctg gccgaggccc 240
agcggggctt tcgggacgca gaggcccagg ctgtcacctg caaccagact gtg 293

<210> SEQ ID NO 11
<211> LENGTH: 20
<212> TYPE: DNA
<213> ORGANISM: Artificial Sequence
<220> FEATURE:
<223> OTHER INFORMATION: dBst-2 F

<400> SEQUENCE: 11
ggtcaggatg gctcctatgc 20

<210> SEQ ID NO 12
<211> LENGTH: 20
<212> TYPE: DNA
<213> ORGANISM: Artificial Sequence
<220> FEATURE:
<223> OTHER INFORMATION: dBst-2 R

<400> SEQUENCE: 12
aacctgacag ggtcacctgg 20

<210> SEQ ID NO 13
<211> LENGTH: 21
<212> TYPE: DNA
<213> ORGANISM: Artificial Sequence
<220> FEATURE:
<223> OTHER INFORMATION: NdBst-2 F

<400> SEQUENCE: 13
gtagccccag ccaaaggttt c 21

<210> SEQ ID NO 14
<211> LENGTH: 20
<212> TYPE: DNA
<213> ORGANISM: Artificial Sequence
<220> FEATURE:

-continued

```
<223> OTHER INFORMATION: NdBst-2 R

<400> SEQUENCE: 14

aggcctcccc atgcccaaac                                                20


<210> SEQ ID NO 15
<211> LENGTH: 19
<212> TYPE: DNA
<213> ORGANISM: Artificial Sequence
<220> FEATURE:
<223> OTHER INFORMATION: AGM-F

<400> SEQUENCE: 15

gagggggaga tctggatgg                                                 19


<210> SEQ ID NO 16
<211> LENGTH: 20
<212> TYPE: DNA
<213> ORGANISM: Artificial Sequence
<220> FEATURE:
<223> OTHER INFORMATION: AGM-R

<400> SEQUENCE: 16

cttctctgca tccagggaag                                                20


<210> SEQ ID NO 17
<211> LENGTH: 180
<212> TYPE: DNA
<213> ORGANISM: Artificial Sequence
<220> FEATURE:
<223> OTHER INFORMATION: Bst-2 mutant 11

<400> SEQUENCE: 17

atggcgccct ctttctatca ctatctgccc gtgcccatgg atgagatggg ggggaagcaa     60

ggatggggca gccaccggca gtggctgggg taccgcggga gaaagatagt gatagacggg    120

aacgggtacc tactctaccc ccccttcgtt cctaccccgt cggtggccgt caccgacccc    180


<210> SEQ ID NO 18
<211> LENGTH: 93
<212> TYPE: DNA
<213> ORGANISM: Artificial Sequence
<220> FEATURE:
<223> OTHER INFORMATION: Bst-2 mutant 12

<400> SEQUENCE: 18

atgtaccgcg ggagaaagat agtgatagac gggaacgggt acctactcta ccccccccttc     60

gttcctaccc cgtcggtggc cgtcaccgac ccc                                 93
```